United States Patent [19]
Lia et al.

[11] Patent Number: 4,762,118
[45] Date of Patent: Aug. 9, 1988

[54] SELF-ADJUSTING STEERING MECHANISM FOR BORESCOPE, ENDOSCOPE, OR GUIDE TUBE

[75] Inventors: Raymond A. Lia, Auburn; Allan I. Krauter, Syracuse, both of N.Y.

[73] Assignee: Welch Allyn, Inc., Skaneateles Falls, N.Y.

[21] Appl. No.: 78,711

[22] Filed: Jul. 28, 1987

[51] Int. Cl.$^4$ .................................................. A61B 1/00
[52] U.S. Cl. .......................................... 128/4; 138/120
[58] Field of Search ............................... 128/4, 5, 6, 7; 138/120

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 3,060,972 | 10/1962 | Sheldon | 138/120 |
| 3,162,214 | 12/1964 | Bazinet, Jr. | 138/120 |
| 3,190,286 | 6/1965 | Stokes | 128/6 |
| 3,266,059 | 8/1966 | Stelle | 138/120 X |
| 3,557,780 | 1/1971 | Sato | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,108,221 | 8/1978 | Freimuth et al. | 141/146 |
| 4,347,837 | 9/1982 | Hosono | 128/6 |
| 4,351,323 | 9/1982 | Ouchi et al. | 128/4 |
| 4,432,349 | 2/1984 | Oshiro | 128/4 |
| 4,651,718 | 3/1987 | Collins et al. | 128/4 |
| 4,655,257 | 4/1987 | Iwashita | 138/120 |

Primary Examiner—William H. Grieb
Attorney, Agent, or Firm—Wall and Roehrig

[57] ABSTRACT

In a cable-steerable endoscope, borescope, or guide tube in which opposing cables are displaced to deflect the tip of the instrument, a self-adjusting mechanism in the control section ensures that a maximal differential force and a minimal total force is applied to the two steering cables. The self-adjusting mechanism has a frame that is affixed within the control section and a slider plate that is slidably disposed on a longitudinal rail of the frame. The slider plate projects outwardly to engage ends of the cable sheaths for the steering cables. The slider plate engages the frame rail when there is force on only one steering cable to lock the slider plate against sliding motion. When there is no force, or equal forces on the steering cables, the slider plate moves proximally on the frame. This arrangement, along with a reset spring, automatically takes up unneeded play or slack in the cables and also avoids the simultaneous tensioning of the two cables that can produce high steering forces and that can damage the steering section.

10 Claims, 2 Drawing Sheets

PROXIMAL ← → DISTAL

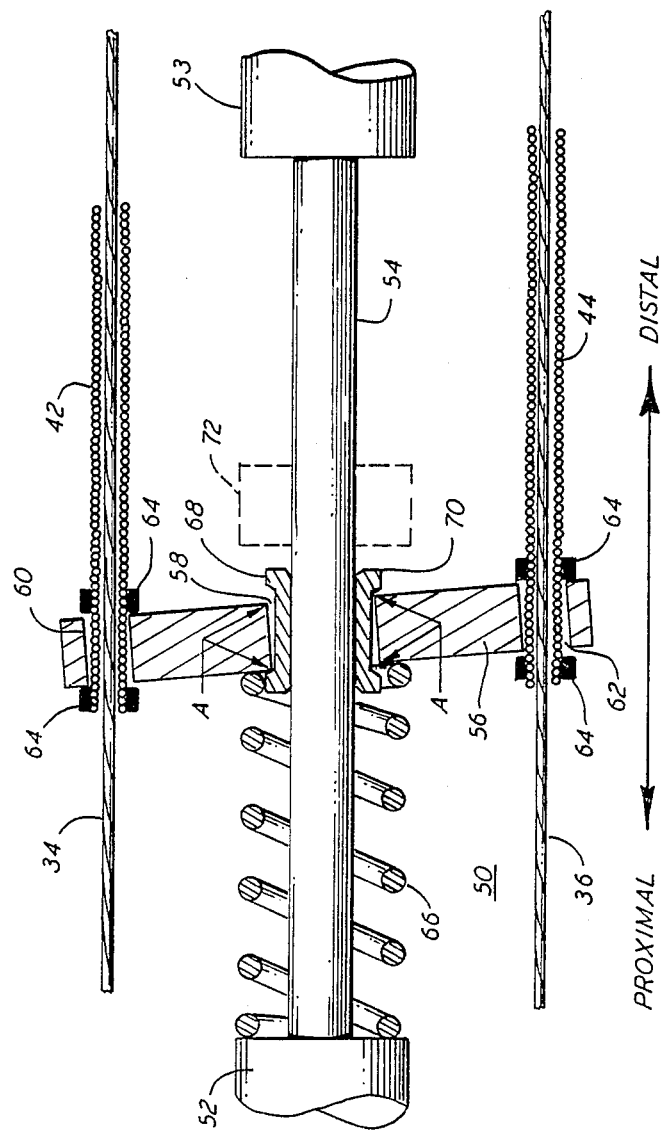

SELF-ADJUSTING STEERING MECHANISM FOR BORESCOPE, ENDOSCOPE, OR GUIDE TUBE

BACKGROUND OF THE INVENTION

This invention relates to a controllably bendable tube assembly, especially a borescope, endoscope, or guide tube of the type having a cable-actuated hollow steering section.

An endoscope is generally characterized as an elongated flexible tube, i.e. an insertion tube, with a viewing head at its distal or forward end, and a control section at its proximal end for controlling or steering the distal end. In such an endoscope, a bendable tube steering section is situated at the distal end adjacent to the viewing head. One or two pairs of control cables extend through the bendable tube section and the remainder of the insertion tube and connect with a steering control in the control section. One or both pairs of these cables are differentially displaced for bending the steering section to facilitate the inspection of an object.

An endoscope is typically inserted into the cavity of a patient in order to visually investigate the tissues within the cavity. For example, an endoscope can be inserted into the colon, stomach, or into the lung of a patient. Because the esophagus, bronchii, and colon are narrow, tortuous passageways, the steering section must be bent rather precisely, and as close to the viewing head as possible, in order to obtain the necessary penetration without damaging the patient's tissues. It is most desirable both that the cable tension be limited and that cable slack be minimized.

A borescope is a similar device, but intended for visual inspection of a mechanical assembly, such as a jet engine or turbine, where it would be difficult or impossible otherwise to examine the assembly's internal elements. The borescope needs to be insertable into narrow tortuous passageways, and must observe similar steering and bending considerations.

A guide tube is similar to a borescope, except that it does not have a viewing head. The guide tube is used for directing the passage of elongated flexible devices into the mechanical assembly.

A number of types of steering mechanisms are known. For example, helically coiled strips are employed in endoscopes or borescopes as described in U.S. Pat. Nos. 3,610,231 and 3,739,770. Articulation sections formed of thin-walled cylindrical segments or bands that are joined by means of pins or bifurcations, or other similar articulations such that the segments are rockable on one another, are described in U.S. Pat. Nos. 3,583,393; 3,669,098; 3,799,151; and 4,347,837. U.S. Pat. No. 3,557,780 describes an endoscope articulation section formed of two flexure portions, with two sets of control wires. Stays or flexible backbone members of various lengths control the degree of curving and the location of the curvature on the articulation section.

An endoscope described in the U.S. Pat. No. 3,799,151 has cylindrical segments articulated in one plane or another plane as required to select the amount and direction of bending of the endoscope articulation section.

For those articulation sections that are bendable in two planes, a significant amount of cable slack is typically included so that the steering cables for one plane do not bind when the articulation section is bent in the other plane. Some cable slack is also included to accommodate cable tightening due to coiling and bending of the insertion tube through which the steering cables pass.

In a steerable endoscope or borescope, opposing steering cables are displaced to deflect its distal tip. These cables are differentially displaced. That is, as one cable is pulled towards the control section, the other moves out from the control section. However, the motion of the one cable is not normally the exact opposite of the motion of the other. Coiling of the insertion tube can result in the tensioning, at the same time, of both cables of an opposed pair. This tensioning increases friction and produces high forces which can damage the articulation section or cables, leading to early failure. Adding cable play or slack can alleviate this problem, but can create other problems of its own, such as imprecise steering. Moreover, large steering knob movements are then required for deflection of the endoscope or borescope tip.

OBJECTS AND SUMMARY OF THE INVENTION

Accordingly, it is an object of this invention to provide a borescope or endoscope which avoids the drawbacks of the prior art.

It is a more specific object of this invention to provide a cable bendable borescope or endoscope that has a minimal amount of slack and that is easy to deflect, even when the insertion tube section is coiled or the steering section is fully deflected in another plane.

It is another object of this invention to minimize or eliminate the need for cable adjustment in endoscopes or borescopes.

It is a further object of this invention to maximize the net or differential force in the opposed pair of steering cables while minimizing the collective or total force in the pair of cables.

It is a still further object of this invention to provide a release mechanism which accomplishes the above objects, but which is simple in design and can be housed in the control section housing.

As aforesaid, the ideal self-adjusting mechanism should ensure that there is maximal differential force and minimal collective force applied to the steering cables of an opposed pair. To achieve this, one of the cables should have zero force during steering. To this end, the self-adjusting mechanism has a frame fixedly mounted within the control section and including a track or rail that is axially oriented, i.e., along the direction of cable motion. A slider is disposed to slide axially along the track or rail, i.e., in the direction of cable motion.

The slider projects outwards and at its lateral extremities engages the ends of the cable sheaths for one set of steering cables. The slider does not interfere with motion of the cables themselves. The slider has a brake mechanism which engages the frame when there is uneven force on the steering cables to lock the slider against sliding motion relative to the frame. When there is significant tension in both cables, the brake releases. This release allows the slider to slide proximally along the frame, which reduces cable tension. A reset spring (or springs) urges the slider distally when no steering forces are present.

In a preferred embodiment, the frame includes a central rod or rail, and the slider is a plate with a central passage that slides on the rail. There are passages at the lateral edges of the plate through which the cable sheaths pass, and these are held by sheath terminators or nuts. When there is a differential force on the cable sheaths, the slider plate pivots or tilts, and edges of its central passage grip the rail. When the forces become substantially equal or disappear, the slider plate becomes free to slide on the rail.

Two separate shoes can be disposed in the central passage between the frame rail and the sides of the central passage to prevent wear on the rail and slider.

The above and many other objects, features, and advantages of this invention will become more fully understood from the ensuing description of a preferred embodiment of the invention.

BRIEF DESCRIPTION OF THE DRAWING

FIG. 3 is a schematic sectional view of a self-adjusting mechanism according to a preferred embodiment of the invention.

DETAILED DESCRIPTION OF THE PREFERRED EMBODIMENTS

Figure 1:
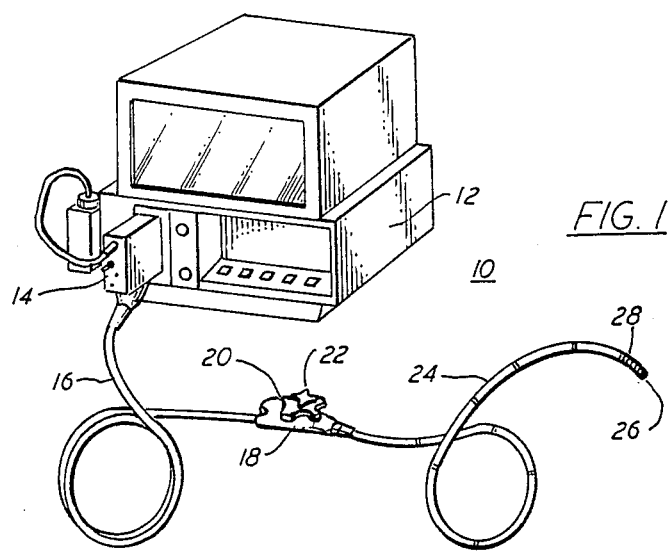
FIG. 1 is a perspective view of a video endoscope of the type which can employ the self-adjusting steering mechanism of this invention.
Figure 2:
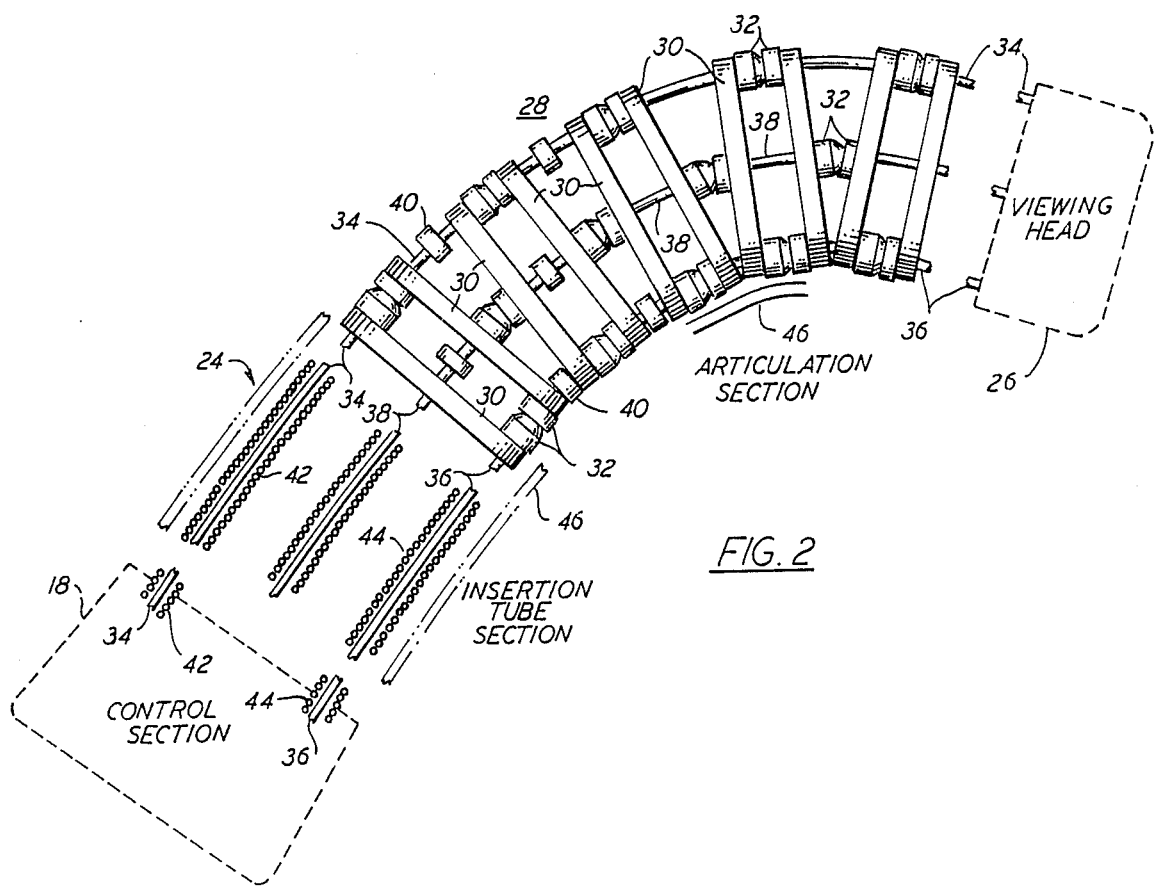
FIG. 2 is a schematic view, partly cut away, of a cable-type articulation section of the endoscope of FIG. 1.

With reference to the drawing, FIG. 1 shows a video endoscope system 10, having a video monitor and console 12, with a connector adaptor 14 that connects the console 12 through an umbilical 16 to an endoscope control unit 18. The control unit 18 has a pair of steering knobs 20 and 22 for deflecting the endoscope tip in the upwards-downwards direction and in the left-right direction, respectively. An elongated flexible insertion tube 24 extends from the control unit and has at its tips a viewing head 26 that contains illuminating and video pick-up devices. Just to the proximal side of the viewing head 26 is a steering section 28 of the cable-actuated type of which an example is shown in FIG. 2. It is noted that many such steering mechanisms exist, as described in the patents identified earlier. Endoscopes of this general design are described e.g., in U.S. Pat. Nos. Re 31,289 and Re 31,290 each of June 28, 1983.

Borescopes are of similar design, but typically with longer insertion tubes.

With reference to FIG. 2, a articulation section 28 is shown of the type described in commonly-assigned U.S. patent applications Nos. 806,667, and 07/078,713.

Other articulated-cable-type steering mechanisms are described in U.S. Pat. Nos. 3,610,231; 3,739,770; 3,583,393; 3,669,098; 3,799,151; 4,347,837; 3,557,780; 3,060,972; 4,108,221; and 3,190,286.

In FIG. 2, the articulation section 28 is formed of a stack of apertured washers 30, sometimes called vertebrae or discs, which are separated by an arrangement of spacer beads 32. To effect upward-downward deflection of the viewing head 26, an upper steering cable 34 and a lower steering cable 36 penetrate through opposite sides of the washers 30 and through the associated spacer beads 32, and are affixed onto the viewing head 26. These cables 34 and 36 extend back through the insertion tube 24 to the control section 18. Also shown is another cable 38 (its opposing associated cable is obscured in this view) for controlling right-to-left steering. Limiter beads 40 are disposed on the cable at selected locations to limit the amount of bending of the articulation section, especially at the proximal end thereof.

Within the insertion tube 24, the cables 34 and 36 run through cable sheaths 42 and 44 respectively. These sheaths are flexible but resist axial compression. Thus, the cable sheaths 42 and 44 provide reaction forces for the forces on the cables 34 and 36, so that any cable motion is transferred from the control section 18 to the articulation section 28.

The flexible insertion tube 24 terminates at the articulation section 28. A flexible outer covering 46 covers the articulation section 28 and is attached to the insertion tube 24 and to the viewing head 26. The cable sheaths 42 and 44 are anchored at the articulation side of the steering section 28 and extend into the control section 18. The cables 34, 36 are themselves anchored in the viewing head 26, and the proximal ends thereof are connected to a windlass arrangement (not shown) in the control section 18.

As shown in FIG. 3, a self-adjusting steering mechanism 50 according to one preferred embodiment of this invention has a frame member 52 affixed inside the housing of the steering section 18. This frame member 52 is composed of a longitudinal rail or rod 54 that extends in the axial direction, i.e., parallel to the cables 34 and 36. A slider plate 56 is fitted onto the frame member 52 to slide on the rail 54, and this plate has a central bore or passage 58 through which passes the rail 54. The slider plate 56 extends laterally outward to or beyond the positions of the steering cables 34 and 36, and has bores or passages 60 and 62 near its periphery through which the cable sheaths 42 and 44 respectively pass. The cable sheaths 42 and 44 are retained in the passages 60 and 62 by cable nuts or terminations 64, disposed on each side of the slider plate 56. Alternatively, the cable sheaths 42, 44 can simply butt against the slider plate 56.

A compression reset spring 66 is placed around the rail 54 and between the frame member 52 and the proximal face of the slider plate 56. This reset spring 66 urges the slider plate 56 distally. Alternatively, a tension spring can be placed around each cable sheath 42, 44. One of these two springs would be attached to the slider plate 56 at the bore 60 and the other spring would be attached to the slider place 56 at the bore 62. The distal ends of the springs would be attached to a distal extension 53 of the frame member 52.

An upper shoe 68 and a lower shoe 70, which are optional, are loosely fitted to the slider plate 56 and fit in the central passage 58 between the walls of the passage and the frame 54. These shoes tend to prevent wear at edge points A of the passage walls.

The exact shapes of slider plate central passage 58 and the cross section of the rail 54 are not critical. However, it is preferred that the rail be a somewhat flattened tongue and the passage be elongated horizontally. This will serve to prevent rotation of the slider plate 56 out of the plane of the cables 34 and 36 and will present a rather broad surface for gripping of the slider plate 56 against the rail 54.

The slider plate 56 can rock somewhat, i.e., can rotate in the plane of the drawing. Rotation clockwise or counterclockwise away from the vertical forces the shoes 68 and 70 against the frame rail 54 and stops motion of the slider plate 56. When the slider plate 56 is more or less vertical, it can be moved freely along the rail 54 by forces of the cable sheaths 42, 44 and of the reset spring 66.

The self-adjusting mechanism 50 operates as described hereafter, considering first, for purposes of illustration, steering in the upward direction (in the drawing) and thereafter steering in the downward direction.

Initially, the upper cable 34 is tightened, which causes the upper sheath 42 to bias against the slider plate 56. The latter rotates counter-clockwise and biases the shoes 68, 70 against the rail 54. This tends to grip the slider plate 56 on the rail 54 and prevent any axial movement of the slider plate 56. If there is no force at this time on the bottom cable 36, the lower cable sheath 44 does not push against the slider plate 56, the shoes 68 and 70 will lock against the frame rail 54, and steering continues. However, if there is a simultaneous force on the lower cable 36, the associated force of the bottom sheath 44 on the slider plate 56 reduces the force of the shoes 68, 70 on the rail 54. This allows the shoes 68, 70 and the slider plate 56 to move proximally on the frame rail 54. As the slider plate 56 moves, the simultaneous force in the lower cable 36 is reduced. When the force in the lower cable 36 becomes small, the force of the bottom sheath 44 against the lower side of the slider plate 56 also becomes small, and a high rocking force resumes on the slider plate 56. The shoes 68 and 70 and slider plate 56 lock onto the frame rail 54, and further motion to the proximal side is prevented. Steering in the upward direction can resume.

From this point, steering in the downward direction first reduces the force on the upper cable 34 and sheath 42. This relieves the gripping of the slider plate 56 and shoes 68, 70 against the rail 54, and the slider plate 56 moves distally under the force of the reset spring 66. When forces appear on the bottom steering cable 36 and bottom sheath 44, the force of the bottom sheath 44 against the slider plate 56 rotates the latter clockwise, and the slider plate 56 and shoes 68, 70 lock onto the frame rail 54. Downward steering then continues. If steering forces appear again on the upper cable 34 and sheath 42, the slider plate 56 is rocked vertical, is released from the rail 54, and can move proximally. Operation for downward steering is substantially the same as for upward steering, as the adjusting mechanism is symmetrical in operation.

With the preferred embodiment described above, steering slack or play is removed, whenever no steering forces exist in cables 34, 36, by motion of the slider plate 56 and shoes 68, 70 distally under the force of reset spring 66. A modification of this preferred embodiment contains stop 72 that is positioned on the rail 54 distally of the slider plate 56. The spring 66 is preloaded by the stop such that the spring force exceeds the usual or typical steering forces that would be encountered by the steering cables 34 and 36. With this modification, steering slack or play will exist, and the mechanism 50 would not be actuated until all this cable slack is used up, which would occur if the insertion tube 24 is tightly coiled, e.g., for storage or shipment. When the insertion tube is completely uncoiled, the steering behaves as through the mechanism 50 were not present.

While the invention has been described in detail with reference to a preferred embodiment, it should be recognized that the invention is not limited only to that embodiment, but that many modifications and variations thereof would be apparent to those of skill in the art without departing from the scope and spirit of the invention, as defined in the appended claims.

What is claimed is:

1. In a steerable endoscope, borescope, or guide tube having a cable-bendable articulation section disposed proximally of its distal tip and including at least one pair of steering cables and bending means responsive to differential movement of the cables to bend the articulation section, a flexible insertion tube section proximally of the articulation section through which said steering cables pass, and a control section proximally of said insertion tube section and which includes means for imparting a differential motion to said steering cables to bend said articulation section, with said steering cables having respective cable sheaths extending thereover from said control section to said articulation section to carry opposing forces to any forces applied to said steering cables;

the improvement wherein said control section includes a self-adjusting articulation mechanism comprising a frame fixedly mounted in said control section and including axially oriented track means; slider means which is axially slidable on said track means, including means extending radially outward from said track means for engaging the proximal ends of said cable sheaths; and engaging means on said slider means for engaging said track means when the forces on said steering cables are unequal to lock the slider means against proximal sliding motion on said frame, but permitting said proximal sliding motion when there are similar tension forces on both said steering cables.

2. The self-adjusting articulation mechanism of claim 1 in which said track means includes a longitudinal rail and said slider means includes a slider plate having a central passage through which said rail passes and a pair of passages disposed at the periphery of said slider plate, through which said cables respectively pass and against which said cable sheaths abut.

3. The self-adjusting articulation mechanism of claim 2 in which said slider plate is biased by said cable sheaths so as to rock when there are uneven forces on said steering cables.

4. The self-adjusting articulation mechanism of claim 2 further comprising shoe means within said slider plate central passage and slidably over said frame rail preventing wear of said slider plate and said rail.

5. The self-adjusting articulation mechanism of claim 4 in which said shoe means include a separate upper shoe and lower shoe.

6. The self-adjusting articulation mechanism of claim 1 further comprising resilient reset means for urging said slider plate distally when there are zero tension forces on both said steering cables.

7. The self-adjusting articulation mechanism of claim 2 further comprising a coil compression reset spring biasing said slider plate distally.

8. The self-adjusting articulation mechanism of claim 2 further comprising two tension reset springs, each positioned around one said steering cable sheath, biasing said slider plate distally.

9. The self-adjusting articulation mechanism of claim 2 wherein said frame has a single longitudinal rail that is in the form of a flattened tongue.

10. The self-adjusting articulation mechanism of claim 2 wherein a stop limits the distal motion of said slider plate.

* * * * *